(12) United States Patent
McDaniels, III

(10) Patent No.: US 6,660,776 B1
(45) Date of Patent: Dec. 9, 2003

(54) COMPOSITION AND METHOD FOR LUBRICATING AND PROTECTING THE ORAL CAVITY USING FLAVORED PETROLEUM JELLY

(75) Inventor: Pellom McDaniels, III, 807 SW. Bishop Dr., Blue Springs, MO (US) 64014

(73) Assignee: Pellom McDaniels, III, Lawrenceville, GA (US)

( * ) Notice: Subject to any disclaimer, the term of this patent is extended or adjusted under 35 U.S.C. 154(b) by 763 days.

(21) Appl. No.: 09/007,424

(22) Filed: Jan. 15, 1998

(51) Int. Cl.⁷ .................. A61K 47/32; A61K 47/00; A01N 25/00
(52) U.S. Cl. ............. 514/772.4; 514/783; 514/969
(58) Field of Search ................. 514/772.4, 783, 514/969, 817; 424/401, 435

(56) References Cited

U.S. PATENT DOCUMENTS

| | | | |
|---|---|---|---|
| 825,268 A | 7/1906 | Eilertsen | 106/35 |
| 3,852,475 A | 12/1974 | Tarangul | 424/361 |
| 3,903,252 A | 9/1975 | Stearns et al. | 424/7 |
| 4,348,378 A | 9/1982 | Kosti | 424/7 |
| 4,474,803 A | 10/1984 | Hall et al. | 424/285 |
| 4,715,369 A | * 12/1987 | Suzuki et al. | |
| 5,057,497 A | 10/1991 | Calam et al. | 514/21 |
| 5,407,678 A | 4/1995 | Rose et al. | 424/401 |
| 5,595,745 A | 1/1997 | Znaiden et al. | 424/401 |
| 5,658,586 A | * 8/1997 | Rajaiah et al. | |
| 5,888,480 A | * 3/1999 | Homola et al. | 424/54 |

OTHER PUBLICATIONS

Copy of Vaseline™ Lip Therapy™ petroleum jelly product packagning, 1980s.*

* cited by examiner

Primary Examiner—Sreeni Padmanabhan
Assistant Examiner—Lauren Q. Wells
(74) Attorney, Agent, or Firm—The Eclipse Group

(57) ABSTRACT

A composition and method for lubricating and protecting the oral cavity generally and specifically the teeth, gums and tongue using a flavored petrolatum. In the preferred embodiment, the composition contains about 96%–98% (w/w) of petrolatum and about 2%–4% (w/w) of flavoring. The composition is liberally applied to the affected areas of the oral cavity to lubricate and protect those areas during dental or medical procedures having an aesthetically pleasing flavor without leaving an undesirable aftertaste.

6 Claims, No Drawings

COMPOSITION AND METHOD FOR LUBRICATING AND PROTECTING THE ORAL CAVITY USING FLAVORED PETROLEUM JELLY

BACKGROUND OF THE INVENTION

This invention relates to a method for lubricating and protecting the oral cavity using a flavored petroleum jelly.

Solid petrolatum or petroleum jelly has been used as a therapeutic agent for topical application to wounds, burns and other affected areas. It is well known that petroleum jelly has lubricating, softening and skin conditioning characteristics.

Among the many attributes of petrolatum which make its use in topical applications advantageous are its hydrophobicity; its adherence characteristics, and its lubricity, consistency and viscosity which permits easy application and desirable film-forming properties. These same attributes are advantageous when petrolatum is used as a lubricant in and around the oral cavity, especially for medical/dental procedures where the health care professional is wearing rubber gloves and does not want the gloves to adhere to the patient's teeth, tongue and gums.

Unflavored petroleum jelly is currently used as a protectant in or around the mouth for dental procedures to protect the lips and gums, or during surgery to the lips, gums and inside of the mouth to serve as a lubricant and protectant when breathing tubes and the like are placed in and around the mouth. The unfortunate side effect of this use of petroleum jelly is the unpleasant aftertaste in the mouth of the patient after the procedure. It is apparent that this problem of unpleasant taste is present whenever petroleum jelly is used in and around the oral cavity. This is true when spreader-type devices are used during medical/dental procedures to maintain the oral cavity in an open position.

In the art of lubricants and protectants, the use of ointments and gels is well known. In the case of anesthetic gels or sexual lubricating gels, however, the gels tend to be water soluble and do not provide adequate protection from drying. Conversely, dental products like anesthetic and antiseptic compositions and plaque disclosing compositions have incorporated flavorings. These compositions, however, are not petrolatum-based, have pharmacologic ingredients and thus do not provide the desired characteristics of a flavored petrolatum for use in the oral cavity. Finally, compositions like lip balm sold under the trademark CHAPSTICK® have flavorings but likewise have additional ingredients such as sunscreens, camphor and menthol, are generally solids rather than an easily applied ointment, and are not used as a protectant and lubricant in the oral cavity.

The present invention solves the need for a lubricant and protectant for use in and around the oral cavity having a pleasing taste for the user. This novel invention combines petroleum jelly and flavoring to create a unique composition for keeping a patient's gums, teeth and areas in, around and surrounding the oral cavity protected, lubricated and/or moisturized.

SUMMARY OF THE INVENTION

It is an object of this invention to provide a method for lubricating and protecting the oral cavity using improved petroleum jelly compositions having a desirable taste.

It is another object of this invention to provide flavored petroleum jelly compositions for use as protectants and lubricants in and around the oral cavity.

The foregoing objects and other features and advantages of the present invention are achieved by a composition comprising approximately 96–98% petrolatum and approximately 2–4% flavoring.

Other objects of this invention will be set forth in, or be apparent from, the following detailed description of the invention.

DETAILED DESCRIPTION OF THE INVENTION

The present invention relates to the composition and use of flavored petroleum jelly containing from approximately 96% to 98% petrolatum and containing from approximately 4% to 2% flavoring.

Petroleum is a semi-solid mixture of hydrocarbons derived by distillation of paraffin-based petroleum fractions. The solid form may be either water-white or pale yellow, either of which may be used in the present invention so long as it is U.S.P., N.F. or F.C.C. grade.

In the preferred embodiment, approximately 96% to 98% petrolatum is combined with 2% to 4% flavoring using a standard geometric dilution process. When a flavoring agent like spearmint is used, approximately 2% spearmint is required to mask the unpleasant taste of approximately 98% petrolatum and create a spearmint tasting protectant ointment. When a flavoring agent like orange citrus, however, is used, approximately 4% orange citrus is required to mask the unpleasant taste of approximately 96% petrolatum and create an orange citrus lubricating and protectant ointment.

Is In the compositions of the invention, numerous other flavorings can be combined with petrolatum in an amount sufficient to mask the undesirable taste of the petrolatum. Other flavorings include peppermint extract, licorice extract, lemon extract, cherry extract and those listed in Remington's Pharmaceutical Sciences, 16th edition, pp. 1230–39 (1980).

Specific embodiments of the ointment compositions prepared in accordance with the present invention are illustrated by the following representative examples. It will be understood, however, that the invention is not confined to the specific limitations set forth in the individual examples, but rather to the scope of the appended claims.

EXAMPLE 1

A flavored petroleum jelly composition for use as a moisturizer or lubricant in and around the oral cavity is prepared as follows: 98.0 parts of petrolatum and 2.0 parts of spearmint extract are mixed by standard geometric dilution process. The resulting ointment composition has the following formulation:

| Ingredient | % W/W |
|---|---|
| Petrolatum | 98.00 |
| Spearmint extract | 2.00 |
| | 100.00 |

The resulting homogeneously mixed ointment was pharmaceutically stable and had an aesthetically pleasing taste.

EXAMPLE 2

A flavored petroleum jelly composition is prepared in accordance with the procedure of Example 1 having the following formulation:

| Ingredient | % W/W |
|---|---|
| Petrolatum | 96.00 |
| Orange citrus | 4.00 |
| | 100.00 |

Like the composition of Example 1, the resulting ointment was stable and had a pleasant taste.

The above compositions are used to lubricate and protect the oral cavity of a patient, particularly the teeth, gums and tongue, by liberally applying the flavored ointment to the affected area using one's fingers or a swab, etc. and uniformly coating those areas. As stated above, the inventive ointment lubricates, moisturizes and protects the oral cavity during medical or dental procedures, especially when latex gloved hands are placed in the patient's mouth. The flavored jelly composition can also be used in performing arts when applied to the teeth of the performer to ease mouth movements in order to enhance smiling.

Various other features and embodiments of the present invention not specifically enumerated will be obvious to those skilled in the art, all of which may be achieved without departing from the spirit and scope of the invention as defined by the following claims.

I claim:

1. A method for protecting a patient's oral cavity by lubricating the oral cavity using a flavored petroleum jelly, comprising the steps of:

preparing a composition containing about 96% to 98% petrolatum jelly by weight of said composition and about 2% to 4% flavoring by weight of said composition; and liberally applying the flavored petroleum jelly composition to the affected area of the oral cavity to lubricate said cavity.

2. The method of claim 1 wherein said composition further comprises about 2% spearmint extract by weight of said composition.

3. The method of claim 1 wherein said composition further comprises about 4% orange citrus by weight of said composition.

4. A method for protecting a patient's oral cavity by lubricating the oral cavity comprising the step of:

liberally applying a flavored petroleum jelly composition containing about 98% petrolatum jelly by weight of said composition and about 2% spearmint by weight of said composition to the oral cavity to lubricate said cavity.

5. A method for protecting a patient's oral cavity by lubricating the cavity comprising the step of:

liberally applying a flavored petroleum jelly composition containing about 96% petrolatum jelly by weight of said composition and about 4% orange citrus by weight of said composition to the oral cavity to lubricate said cavity.

6. A method for protecting a patient's oral cavity from injury associated with medical or dental procedures by lubricating the oral cavity using a flavored petroleum jelly, comprising the steps of:

preparing a composition containing about 96% to 98% petrolatum jelly by weight of said composition and about 2% to 4% flavoring by weight of said composition; and liberally applying the flavored petroleum jelly composition to the area of the oral cavity to be affected by the medical or dental procedure to lubricate said cavity and protect said cavity from injury associated with the medical or dental procedure.

* * * * *